United States Patent [19]

Lacroix et al.

[11] 4,021,549

[45] May 3, 1977

[54] FUNGICIDAL COMPOSITIONS BASED ON MONOAMINOPHOSPHITES

[75] Inventors: Guy Lacroix; Jean-Claude Debourge, both of Lyon, France

[73] Assignee: Philagro, France

[22] Filed: Apr. 3, 1975

[21] Appl. No.: 564,592

[30] Foreign Application Priority Data

Apr. 10, 1974 France .............................. 74.13246

[52] U.S. Cl. .............................. 424/220; 424/200; 424/209
[51] Int. Cl.² ............................................. A01N 9/36
[58] Field of Search .................... 260/959; 424/220

[56] References Cited

UNITED STATES PATENTS 3,832,424 8/1974 Freenor .............................. 260/959

OTHER PUBLICATIONS

Houben–Weyl, vol. XII–2, pp. 99 to 102.
Lucas et al., J. Am. Chem. Soc., 72, (1950), pp. 5491–5496.

Primary Examiner—V. D. Turner
Attorney, Agent, or Firm—Robert E. Burns; Emmanuel J. Lobato; Bruce L. Adams

[57] ABSTRACT

Fungicidal monoaminophosphite compositions are described. Methods of treatment of commercial plants susceptible to fungal infections such as mildew are described. The compositions are non-phytotoxic and are effective by systemic and topical application.

9 Claims, No Drawings

FUNGICIDAL COMPOSITIONS BASED ON MONOAMINOPHOSPHITES

FIELD OF THE INVENTION

This invention relates to fungicidal compositions based on substituted monoaminophosphites.

THE INVENTION

More particularly, the invention relates to compositions which are suitable for use in controlling parasitic fungi, especially mildews, in plants and which contain as active material a compound corresponding to the general formula

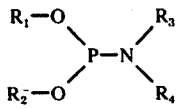

in which $R_1$ and $R_2$, which may be the same or different, each represent an optionally halogenated or hydroxylated linear or branched alkyl radical or group containing 1 to 10 carbon atoms, the carbon chain optionally being interrupted by an oxygen or sulphur atoms, or an alkenyl or alkinyl radical containing 2 to 5 carbon atoms, in addition to which $R_1$ and $R_2$ may also form, with the oxygen and phosphorus atoms, a 5-membered or 6-membered ring, optionally substituted by alkyl radicals containing from 1 to 3 optionally halogenated carbon atoms, halogens or alkoxy alkyl radicals with 1 to 5 carbon atoms, the ring optionally being attached to a phenyl radical through a carbon-carbon bond, $R_3$ and $R_4$, which may be the same or different, each represent hydrogen, an alkyl, alkenyl, alkinyl or alkoxy radical, the hydrocarbon portion of these radicals containing from 1 to 5 carbon atoms, or together with the nitrogen atom may form a 6-membered heterocyclic ring.

The invention also relates to fungicidal compositions containing as active material a metal complex of one of the compounds defined above. Metals which may be used in complexes of this kind include, in particular, the alkali and alkalineearth metals, zinc, manganese, magnesium and copper.

BACKGROUND OF THE INVENITON

Although, many of these compounds are known per se, the literature does not indicate that they show fungicidal properties. The general methods for synthesising these compounds are described in Houben-Weyl, Vol. XII/2, pages 99 to 102.

The most widely used synthesis comprises reacting an optionally cyclic diester chloride of phosphorous acid with a primary or secondary amine in a solvent medium in accordance with the method developed by LUCAS, MITCHELL, SCULLY (J. Am. Chem. Soc. 72, pp. 5491–6/1950). 2-(N,N-dimethylamino)-1,3,2-dioxaphospholane for example may be prepared in this way.

23.5 g (0.2 M) of 2-chloro-1,3,2-dioxaphospholane are dissolved in 100 ml of petroleum ether. The solution is cooled to below 20° C and 18 g (0.4 M) of dimethylamine dissolved in 50 ml of petroleum ether are run in while stirring, the temperature being kept between −20° and −10° C. After the dimethylamine solution has been run in, the temperature is allowed to rise again and the dimethyl ammonium hydrochloride is filtered. The petroleum ether is removed, leaving an oil which is distilled in a water-jet pump vacuum.

b.p.$_{15}$: 64–66° C, $n_D^{20}$ = 1.4715, yield: 67%

| Analysis | C % | H % | N % | P % |
|---|---|---|---|---|
| Calculated | 35.6 | 7.42 | 10.32 | 22.95 |
| Found | 35.76 | 7.18 | 10.33 | 22.88 |

The compounds whose characteristics are shown in the following Table were similarly prepared:

| Compounds | Physical characteristics | Yield |
|---|---|---|
| O,O-diethyl-N,N-diethyl-aminophosphite | b.p.:70–80°C/15mmHg | 22 % |
| 2-(N,N-diethylamino)-1,3,2-dioxaphospholane | b.p.:87–88°C/16mmHg $n_D^{20}$ = 1.469 | 58 % |
| 2-(N-isopropylamino)-1,3,2-dioxaphospholane | b.p.:75°C/15mmHg $n_D^{20}$ = 1.469 | 47 % |
| 2-(N,N-diisopropylamino)-1,3,2-dioxaphospholane | b.p.:95–97°C/15mmHg $n_D^{20}$ = 1.464 | 27 % |
| 2-(N,N-diallylamino)-1,3,2-dioxa-phospholane | b.p.:105°C/14mmHg | 62 % |
| 2-(1-piperidyl)-1,3,2-dioxa-phospholane | b.p.:62–64°C/0.04mmHg | 63 % |
| 2-(1-morpholinyl)-1,3,2-dioxa-phospholane | b.p.:116–117°C/7mmHg m.p.: 32–32.5°C | 67 % |
| 2-(N,N-diethylamino)-4-methyl-1,3,2-dioxaphospholane | b.p.86–87°C/13mmHg $n_D^{20}$ = 1.461 | 64 % |
| 2-(1-morpholinyl)-4-methyl-1,3,2-dioxaphospholane | b.p.117–120°C/10mmHg $n_D^{20}$ = 1.4928 | 40 % |
| 2-(N,N-diethylamino)-4-methoxy methyl-1,3,2-dioxaphospholane | b.p.77°C/0.2mmHg $n_D^{20}$ = 1.4649 | 80 % |
| 2-N,N-(diethylamino)-4,5-benzo-1,3,2-dioxaphospholane | b.p.:68–76°C/0.04mmHg $n_D^{20}$ = 1.5318 | 78 % |
| 2-(N,N-diethylamino)-1,3,2-dioxaphosphorinane | b.p.:87°C/15mmHg | 61 % |
| 2-(N,N-di-n-butylamino)-5,5-dimethyl-1,3,2-dioxa-phosphorinane | b.p.:84°C/0.01mmHg $n_D^{20}$ = 1.4655 | 73 % |

These compounds may form complexes with certain metal salts. The fungicidal application of these complexes is also part of the invention. Thus, a complex of cuprous chloride and 2-(N,N-diethylamino)-1,3,2-dioxaphospholane was prepared as follows:

1.0 g of cuprous chloride is added under a $CO_2$ atmosphere to 1.6 g of 2-(N,N-diethylamino)-1,3,2-dioxaphospholane. The temperature of the mixture rises to 100° C. Recrystallisation from alcohol gives 0.9 g of a white product. Yield: 35%, m.p. 121–122° C.

| Centesimal analysis for $C_6H_{14}ClCuNO_2P$ | | |
|---|---|---|
| % | Cl | P |
| Calculated | 13.53 | 11.81 |
| Found | 13.48 | 12.04 |

It has also been found that the aminophosphites according to the invention can be hydrolysed to form ammonium salts of monoalkyl phosphites in accordance with the following scheme:

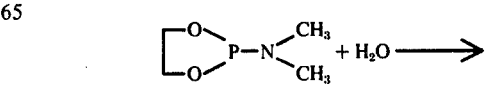

-continued

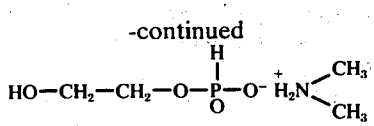

These β-hydroxy ethyl phosphite salts are also fungicidal and are the subject of French Patent Application for Patent of Addition No. 73-37.994.

DETAILS OF THE INVENTION

The following Examples illustrate the fungicidal properties of the compounds listed below:
1-0,0-diethyl-N,N-diethylaminophosphite
2-2-(N,N-dimethylamino)-1,3,2-dioxaphospholane
3 2-(N,N-diethylamino)-1,3,2-dioxaphospholane
4-complex of compound 2 with cuprous chloride
5-2-(N-isopropylamino)-1,3,2-dioxaphospholane
6-2-(N,N-diisopropylamino)-1,3,2-dioxaphospholane
7-2-(N,N-diallylamino)-1,3,2-dioxaphospholane
8-2-(1-piperidyl)-1,3,2-dioxaphospholane
9-2-(1-morpholinyl)-1,3,2-dioxaphospholane
10-2-(N,N-diethylamino)-4-methyl-1,3,2-dioxaphospholane
11-2-(1-morpholinyl)-4-methyl-1,3,2-dioxaphospholane
12-2-(N,N-diethylamino)-4-methoxymethyl-1,3,2-dioxaphospholane
13-2-(N,N-diethylamino)-4,5-behzo-1,3,2-dioxaphospholane
14-2-(N,N-diethylamino)-1,3,2-dioxaphosphorinane.

EXAMPLE 1:

In vivo test on Plasmopara viticola in plants
(a) Preventive treatment
Using a spray gun, the leaves of pot-grown vine plants (Gamay variety) are sprayed underneath with 40 cc of an aqueous suspension of a wettable powder with the following composition (by weight):
active material to be tested 20%
deflocculant (calcium lignosulphate) 5%
wetting agent (sodium alkylaryl sulphonate) 1%
filler (aluminium silicate) 74%
in the required dilution containing the active material to be tested in the dose in question. Each test was repeated three times.

After 48 hours, the plants are contaminated by spraying the leaves underneath with an aqueous suspension containing approximately 80,000 units per cc of spores of the fungus.

The pots are then placed for 48 hours in an incubation cell at 20° C/100% relative humidity.

The plants are examined 9 days after infestation.

Under these conditions, it is found that, in a dose of 0.5 g/l, compounds 1, 2, 3, 4, 5, 6, 7, 9, 11 and 14 afford complete protection, whilst compounds 8 and 13 afford good protection.

In addition, none of the compounds tested showed the least sign of phytotoxicity.

(b) Treatment after contamination
The procedure is as in paragraph (a) above, except that the plants are first contaminated and then treated with the active material to be tested, being examined 9 days after contamination.

Under these conditions, it is found that, in a dose of 40 cc of 1 g/l, compounds 1 and 4 completely stop the development of the mildew in the vine plants.

EXAMPLE 2

Systemic test by root absorption on mildew of the vine

Several vine stocks (Gamay variety), each accommodated in a pot filled with vermiculite and a nutrient solution, are sprayed with 40 cc of a solution containing 0.5 g/l of the material to be tested. After 2 days, the vine is contaminated with an aqueous suspension containing 100,000 spores/cc of Plasmopara viticola. This is followed by incubation for 48 hours in a room at 20° C/100% relative humidity. The degree of infestation is assessed after about 9 days in relation to an infested control which has been sprayed with 40 cc of distilled water.

Under these conditions, it is found that, in this dose of 0.5 g/l, compounds 2 to 14, which are absorbed by the roots, afford complete protection to the vine leaves against mildew, which clearly demonstrates the systemic nature of these compounds.

EXAMPLE 3

Systemic test by leaf absorption on mildew of the vine

Vine stocks (Gamay variety), each accommodated in a pot filled with a mixture of clean soil and sand, are treated at the 7-leaf stage.

The treatment is carried out by spraying the lowest 4 leaves underneath with a wettable powder containing 2.5 g/l of the active material to be tested.

After 2 days, the vine is contaminated with an aqueous suspension containing approximately 100,000 spores per cc of Plasmopara viticola. This is followed by incubation for 48 hours in a room at 20° C/100% relative humidity. The degree of infestation is assessed after about 9 days from the fifth to seventh leaves from the bottom in relation to a control which has been treated with distilled water.

Under these conditions, it is found that compounds 1, 2, 3, 4, 5, 8, 9 and 14 afford total protection, whilst compounds 7, 11 and 13 afford good protection to the upper leaves of the vine against mildew.

EXAMPLE 4

Open-air test on mildew of the vine
Groups of vine stocks (Gamay variety) are naturally infested at the beginning of August after heavy rainfall and frequent watering. These groups of vine stocks are then treated after 8, 14 and 23 days, respectively, with 50% wettable powder sprays containing as active material compound no. 1, manganese ethylene-1,2-bis-dithiocarbamate or manebe and a mixture of these two compounds, respectively.

The following Table shows the results of examinations made 2, 8, 20, 35 and 45 days, respectively, after the last treatment. These results are expressed as percentage protection in relation to a contaminated, but untreated control.

| Active material | dose g/l | Examination after | | | | |
| --- | --- | --- | --- | --- | --- | --- |
| | | 2 days | 8 days | 20 days | 35 days | 40 days |
| compound no. 1 | 2 | 100 | 70 | 15 | 10 | 0 |
| manebe | 1.2 | 95 | 93 | 88 | 77 | 70 |
| compound no. 1 | 2 + 1.2 | 100 | 100 | 100 | 95 | 90 |

-continued

| Active material | dose g/l | Examination after |
| --- | --- | --- |
| | | 2 days / 8 days / 20 days / 35 days / 40 days |
| + manebe | | |

This Table clearly demonstrates the excellent immediate effect of compound no. 1, the remarkable persistence of the mixture (which is better than that of manebe on its own) and, finally, the non-phytotoxicity of compound no. 1 on vine.

EXAMPLE 5

In vitro test on mycelian growth

The compounds according to the invention are tested for their effect on the mycelian growth of the following fungi:

*Rhizoctonia solani*, responsible for canker of the neck,
*Fusarium oxysporum*, responsible for tracheomycosis,
*Fusarium nivale*, responsible for the damping off of seedlings of cereal crops,
*Fusarium roseum*, responsible for fusariosis in cereal crops,
*Sclerotinia minor*, responsible for sclerotiniosis,
*Sclerotinia sclerotiorum*, responsible for sclerotiniosis,
*Pythium de Baryanum*, responsible for the damping off of seedlings,
*Phomopsis viticola*, responsible for excoriosis,
*Septoria nodorum*, responsible for septoriosis in cereal crops,
*Helminthosporium*, responsible for helminthosporiosis,
Verticillium, responsible for verticilliosis,
*Cercospora beticola*, responsible for cercosporiosis.

The "Agar Plate dilution" method is used for each test. A mixture of gelose and an acetone solution or a wettable powder containing the active material to be tested in a concentration of 0.25 g/l is poured into a Petri dish at a temperature of approximately 50° C.

The wettable powder is prepared by mixing the following ingredients for 1 minute in a blade mill:
active material to be tested 20%
deflocculant (calcium lignosulphate) 5%
wetting agent (sodium alkylaryl sulphate) 1%
filler (aluminium silicate) 74%

This wettable powder is then mixed with a quantity of water sufficient for one application in the required dose.

The gelose-containing mixture is left to harden and discs of a mycelian culture of the fungus are placed on it.

A Petri dish similar to the first, except that its gelose medium does not contain any active material, is used as control.

After 4 days at 20° C, the surface area of the inhibition zone observed is evaluated and expressed as a percentage of the inoculated surface.

| Fungus | % inhibition Compound no. 1 |
| --- | --- |
| *Rhizoctonia* | 50 |
| *Fusarium oxysporum* | 60 |
| *Fusarium nivale* | 65 |

-continued

| Fungus | % inhibition Compound no. 1 |
| --- | --- |
| *Fusarium roseum* | 70 |
| *Sclerotinia minor* | 100 |
| *Sclerotinia sclerotiorum* | 50 |
| *Pythium* | 100 |
| *Phomopsis* | 50 |
| *Septoria* | 70 |
| *Helminthosporium* | 70 |
| *Verticillium* | 100 |
| *Cercospora* | 90 |

EXAMPLE 6

In vivo test on living organs:
Test on tomato mildew (Phytophtora infestans)

A drop of a mixture of a suspension of spores containing approximately 80,000 units per cc, and of a suspension in the required dilution of a wettable powder of the same composition as in Example 1 in the case of an insoluble product, or of an acetone solution, is applied to freshly cut tomato leaves.

Under these conditions, compound no. 1 affords complete protection in a dose of 0.5 g/l.

EXAMPLE 7

Tobacco test

Plots of 5 tobacco plants (PB 91) are treated on the 15th June with a wettable powder containing an active material of which 80% consists of manebe (160 g/l) and 50% of compound no. 1 (200 g/l). One plot is left untreated as control.

After 48 hours, the plants are artificially contaminated (with *Peronospora tabacina*) and then fumigated. The treatments are then repeated once weekly.

The plants are then examined on the 12th August by counting the patches of mildew per plot. The results are set out in the following Table:

| PRODUCT | Patches of mildew per plot |
| --- | --- |
| Control | 48 |
| Manebe | 4 |
| Compound no. 1 | 2 |

Other tests have shown that the compound according to the invention is also effective against the same fungus in curative treatment and has a systemic action.

EXAMPLE 8

Avocado test

Avodado plants (variety *Persea indica*) are planted in soil infested with *Phytophtora cinnamomi*, after which the soil is sprayed with a solution containing 3 g/l of compound no. 1. A few plants are left untreated as controls. Under these conditions, it is found after 20 days that the roots of the controls are completely destroyed, while 90% of the roots of the treated plants are healthy.

EXAMPLE 9

Pineapple test

Pineapple plants are contaminated with *Phytophtora parasitica* and then treated after 48 hours by spraying with a solution containing 0.5 g/l of compound no. 1. After 30 days, the treated plants are found to be completely free from the fungus, whilst the controls are infested.

EXAMPLE 10

Strawberry test

Ten strawberry plants (Surprise des Halles variety) are treated by soaking for 1 hour in an aqueous solution containing 0.2% of compound no. 1, dried and planted out on the 14th June, in soil artifically contaminated with *Phytophtora cactorum*. Immediately afterwards, and then once every 8 days until the 18th July, the plants are sprayed with the same solution which corresponds to a total application of 0.5 g of active material per plant.

Plants are treated by soaking and spraying with water to serve as controls.

Under these conditions, it is found on the 24th July that the protection of the strawbery plants is complete, whereas 76% of the control plants are dead.

EXAMPLE 11

Pimento test

Ten pimento plants (Yolo wonder variety) which have already been planted are transplanted on the 27th June into pots of soil artificially contaminated with *Phytophtora capsici*. Immediately afterwards, and then once every 8 days until the 18th July, the plants are sprayed with an aqueous solution containing compound no. 1, corresponding to a total application of 0.5 g of treatment per plant.

Plants are sprayed with water to serve as controls.

Under these conditions, it is found that the treated plants are healthy at the end of August, whilst the control plants are dead by the 25th July.

All these Examples clearly demonstrate the remarkable fungicidal activity of the compounds according to the invention both in preventing and in stopping the development of fungi belonging to various families, such as, in particular, ascomycetes (Fusarium sp . . . ), basidiomycetes (Rhizoctonia sol . . . ) and, above all, the phycomycetes with, in particular, mildew of the vine, tobacco and hops, phytophtora, and also in preventing and stopping the development of soil fungi, such as pythium sp.

This protection may be obtained both for plants grown in temperate climates and for plants grown in tropical climates, such as hops, market-gardening cultures, ornamental plants, soya, citrus fruits, cacao trees, coconut palms, hevea, etc.

In addition, these compounds may advantageously be used in admixture with one another or with other known fungicides, such as metal dithiocarbamates (manebe, zinebe, mancozebe), basic salts or hydroxides of copper (oxychloride, oxysulphate), (tetrahydro)-phthalimides (captane, captafol, folpel), methyl-N-(1-butyl carbamoyl)-2-benzimidazole carbamate (benomyl), 1,2-di-(3-methoxy or ethoxy carbonyl-2-thioureido) benzenes (thiophanates), methyl-2-benzimidazole carbamate, etc., either to complete the range of activity of the compounds according to the invention or to increase their persistence.

It has also been found that these compounds may be mixed with other fungicidal anti-mildew phosphorus derivatives, more especially the optionally substituted 2-hydroxy-1,3,2-dioxaphospholanes which are the subject of Frech Pat. Applications 73-01.803 and 73-37.994, and with phosphorous acid and its salts as disclosed in French Patent Application 73-43.081, the phosphonic monoesters and their salts which are the subject of French Patent Application 73-45.627 and the phosphonic diesters which are the subject of French Patent Application 74-08.995.

The doses in which the compounds are used may vary within wide limits both in dependence upon the virulence of the fungus and in dependence upon the climatic conditions. Generally, doses of from 0.01 to 5 g/l of active material are perfectly adequate.

For their practical application, the compounds according to the invention are rarely used on their own. More often they are part of formulations which generally contain a support and/or surfactant in addition to the active material according to the invention.

In the context of the invention, a "support" is a natural or synthetic organic or mineral material with which the active material is associated to facilitate its application to the plant, to seeds or to soil, or its transportation or handling. The support may be solid (clays, natural or synthetic silicates, resins, waxes, solid fertilisers . . . ) or fluid (water, alcohols, ketones, petroleum fractions, chlorinated hydrocarbons, liquefied gases).

The surfactant may be an ionic or non-ionic emulsifier, dispersant or wetting agent such as, for example, salts of polyacrylic acids, lignin sulphonic acids, condensates of ethylene oxide with fatty alcohols, fatty acids or fatty amines.

The compositions according to the invention may be prepared in the form of wettable powders, dusting powders, granulates, solutions, emulsifiable concentrates, emulsions, suspended concentrates and aerosols.

The wettable powders are normally prepared in such a way that they contain from 20 to 95% of active material, and they generally contain, in addition to a solid support, from 0 to 5% by weight of a wetting agent, from 3 to 10% by weight of a dispersant and, when necessary, from 0 to 10% by weight of one or more stabilisers and/or other additives, such as penetration agents, adhesives or antilumping agents, colorants, etc. The composition of a wettable powder is shown by way of example below:
active material 50%
calcium lignosulphate (deflocculant) 5%
anionic wetting agent 1%
antilumping silica 5%
kaolin (filler) 39%

Aqueous dispersions and emulsions, for example compositions obtained by diluting with water a wettable powder or an emulsifiable concentrate according to the invention, are included within the general scope of the invention. These emulsions may be of the water-in-oil type or of the oil-in-water type and they may have a thick consistency resembling that of a "mayonnaise".

The compositions according to the invention may contain other ingredients, for example protective colloids, adhesives or thickeners, thixotropic agents, stabilisers or sequestrants and other active materials known to show pesticidal properties, especially acaricides or insecticides. The combination of the fungicidal compounds with the insecticides is particularly useful in controlling fungal diseases as insects are a prime vector of such diseases. The term "control" as herein used is used in the sense of the US Agricultural Acts 7 USC 135 and 148.

The above detailed description and examples are merely illustrative of presently preferred modes of practicing the invention. All equivalents mentioned or art-recognized are intended for inclusion in the practice of this invention.

We claim:

1. A process for controlling fungus diseases in susceptible plants, which comprises application to the plant surfaces or the adjacent environment thereof, of a fungicidally effective amount of a composition containing as an active fungicidal agent a monoaminophosphite of the formula:

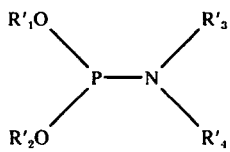

in which
R′$_1$ and R′$_2$, which may be the same or different, each represent a linear or branched alkyl radical containing from 1 to 4 carbon atoms; R′$_3$ and R′$_4$ which independently represent hydrogen or an alkyl radical with 1 to 5 carbon atoms or alkenyl radical with 2 to 3 carbon atoms; or metal complexes thereof with metals selected from the group consisting of alkali or alkaline earth metals, zinc, mangenese, magnesium, and copper; in an agriculturally acceptable carrier, for a preventive or curative treatment.

2. The process for controlling fungus diseases according to claim 1 wherein the active aminophosphite is in the copper complex form.

3. The process for controlling fungus diseases according to claim 1 wherein the fungicidally active aminophosphite is 0,0-diethyl-N,N-diethyl-aminophosphite.

4. The process according to claim 1 for controlling fungus diseases is susceptible plants wherein said diseases are caused by fungi of the phycomycetes family.

5. The process according to claim 1 wherein said fungus disease is mildew of grape vines.

6. The process according to claim 1 for controlling fungus disease in susceptible plants wherein said fungus disease is caused by fungi of the ascomycetes family.

7. The process according to claim 1 for controlling fungus disease in susceptible plants wherein said fungus disease is caused by fungi of the basidiomycetes family.

8. The process according to claim 1 wherein said composition is systemically applied.

9. The process according to claim 1 wherein said composition is topically applied.

* * * * *